United States Patent
Dedroog et al.

(10) Patent No.: US 10,980,427 B2
(45) Date of Patent: Apr. 20, 2021

(54) METHOD AND APPARATUS FOR FULL-SYSTEM, CARDIOVASCULAR SIMULATION AND PREDICTION

(71) Applicant: Dextera Medical, Oslo (NO)

(72) Inventors: Frank Dedroog, Barcelona (ES); Javier Murillo-Castarlenas, Saragossa (ES); Pilar Garcia Navarro, Saragossa (ES); Adrian Navas-Montilla, Saragossa (ES); Jose Ramirez-Rodriguez, Saragossa (ES)

( * ) Notice: Subject to any disclaimer, the term of this patent is extended or adjusted under 35 U.S.C. 154(b) by 305 days.

(21) Appl. No.: 16/016,196

(22) Filed: Jun. 22, 2018

(65) Prior Publication Data
US 2019/0000325 A1 Jan. 3, 2019

Related U.S. Application Data

(60) Provisional application No. 62/523,445, filed on Jun. 22, 2017, provisional application No. 62/530,898,
(Continued)

(51) Int. Cl.
*A61B 5/021* (2006.01)
*A61B 5/02* (2006.01)
(Continued)

(52) U.S. Cl.
CPC ............ *A61B 5/021* (2013.01); *A61B 5/0205* (2013.01); *A61B 5/02007* (2013.01);
(Continued)

(58) Field of Classification Search
CPC .............. G09B 23/303; A61B 5/02007; A61B 5/02028; A61B 5/02042; A61B 5/0205; A61B 5/021
See application file for complete search history.

(56) References Cited

U.S. PATENT DOCUMENTS

| | | | |
|---|---|---|---|
| 9,087,147 B1* | 7/2015 | Fonte | A61B 8/02 |
| 2004/0122294 A1* | 6/2004 | Hatlestad | A61B 5/0205 600/300 |

(Continued)

OTHER PUBLICATIONS

Broome et al., Closed-loop real-time simulation model of hemodynamics and oxygen transport in the cardiovascular system, BioMedical Engineering OnLine 2013, 12:69, http://www.biomedical-engineering-online.com/content/12/1/69 (Year: 2013).*
(Continued)

*Primary Examiner* — Eddy Saint-Vil
(74) *Attorney, Agent, or Firm* — RosserIP, LLC; Roy Rosser

(57) ABSTRACT

A system and method for real-time, a closed-loop, complete body hemodynamic simulation of a patient undergoing a surgical procedure is disclosed. A simplified model of blood circulation that is nevertheless comprehensive and derives input representative of the patient's entire circulatory system, is mathematically modeled by a combination of 1-D mathematical models, and lumped parameter models. The system allows a clinician to select an intended intervention that is then computationally simulated in real, or quasi-real, time. The results of the simulation are presented as a heartbeat by heartbeat simulation of clinician selected, relevant hemodynamic parameters, allowing the clinician to decide whether or not to proceed with the intervention. The system includes accurate simulation of the effects of gravity, respiration and natural compensatory mechanisms, including the baroreflex.

10 Claims, 4 Drawing Sheets

Related U.S. Application Data filed on Jul. 11, 2017, provisional application No. 62/577,466, filed on Oct. 26, 2017, provisional application No. 62/688,686, filed on Jun. 22, 2018.

(51) Int. Cl.
  *A61B 5/0205* (2006.01)
  *G09B 23/30* (2006.01)

(52) U.S. Cl.
  CPC ...... *A61B 5/02028* (2013.01); *A61B 5/02042* (2013.01); *G09B 23/303* (2013.01)

(56) References Cited

U.S. PATENT DOCUMENTS

| | | | |
|---|---|---|---|
| 2007/0014452 A1* | 1/2007 | Suresh | A61B 90/36 382/128 |
| 2012/0179007 A1* | 7/2012 | Rinehart | A61B 5/4833 600/301 |
| 2013/0211247 A1* | 8/2013 | Kalafut | A61B 6/507 600/432 |
| 2015/0065846 A1* | 3/2015 | Choi | A61B 5/02007 600/407 |
| 2015/0324962 A1* | 11/2015 | Itu | A61B 5/02028 382/130 |
| 2015/0374300 A1* | 12/2015 | Najarian | A61B 5/7253 604/66 |
| 2016/0196384 A1* | 7/2016 | Mansi | A61B 5/0205 600/301 |
| 2017/0329905 A1* | 11/2017 | Passerini | G06N 20/00 |

OTHER PUBLICATIONS

Mossa et al., Engineering Modeling of Human Cardiovascular System, the 1st Regional Conference of Eng. Sci. NUCEJ Spatial Issue vol. 11, No. 2, pp. 307-314, 2008 (Year: 2008).*

Liang et al. A closed-loop lumped parameter computational model for human cardiovascular system, JSME International Journal (C), 48 (2005), pp. 484-493 (Year: 2005).*

Lin et al., High-resolution Roe's scheme and characteristic boundary conditions for solving complex wave reflection phenomena in a tree-like arterial structure, Journal of Computational Physics, vol. 260, pp. 143-216, 2014 (Year: 2014).*

\* cited by examiner

METHOD AND APPARATUS FOR FULL-SYSTEM, CARDIOVASCULAR SIMULATION AND PREDICTION

CROSS-REFERENCE TO RELATED APPLICATIONS

This application claims priority to U.S. Provisional Patent Application Ser. No. 62/688,686 filed Jun. 22, 2018 entitled "Simplified Closed Loop Cardio Simulator", U.S. Provisional Patent Application Ser. No. 62/577,466 filed Oct. 26, 2017 entitled "Closed Loop Cardio Simulator", U.S. Provisional Patent Application Ser. No. 62/530,898 filed Jul. 11, 2017 entitled "Exact Energy Balance Solver", U.S. Provisional Patent Application Ser. No. 62/523,445 filed Jun. 22, 2017 entitled "Global Multiscale Human Circulation Simulator", the contents of all of which are fully incorporated herein by reference.

BACKGROUND OF THE INVENTION

(1) Field of the Invention

The invention relates to a system and method for simulating, and for predicting, patient specific hemodynamic parameter values, as computed from pressure, velocity and blood flow data, to aid the evaluation of vascular and ventilation systems, and more particularly, to the real-time simulation and predication of such hemodynamic parameter values to aid qualified clinicians in evaluating intended surgery related interventions before, and during, the performance of such interventions.

(2) Description of the Related Art

The technical problem of predicting the consequences of surgical, or medicinal, interventions is inherent in the technical fields of medicine and surgery. It would, for instance, be of considerable use for a surgeon, or other trained clinician, to be able to accurately predict the actual consequences of an intended action before the action is taken. If such predictions could be made in real, or quasi-real time, they would be of especial interest in operating room, or emergency room, settings where life altering decisions often need to be made under considerable time pressure.

While mathematically based cardio-vascular simulation and prediction systems exist, the relevant prior art often focuses on specific regions of the overall human hemodynamic system, as in, for instance, U.S. Pat. No. 9,226,672 issued to Taylor on Jan. 5, 2016 entitled "Method and system for patient-specific modeling of blood flow" that describes a system for determining cardiovascular information for a patient. This patent discloses a computer system configured to receive patient-specific data regarding a geometry of the patient's heart, and create a three-dimensional model representing at least a portion of the patient's heart based on the patient-specific data. The disclosed system may also be configured to create a physics-based model relating to a blood flow characteristic of the patient's heart and determine a fractional flow reserve within the patient's heart based on the three-dimensional model and the physics-based model.

The human hemodynamic system is complex and includes many compensatory mechanisms, such as, but not limited to, the negative feedback loop of the baroreflex, that may interact with any interventions, be they surgical, medicinal or merely mechanical such as, but not limited to, a change in patient orientation, or applied pressure to an organ.

A full-system, closed loop cardiovascular simulation and prediction system is, therefore, a requirement for meaningfully accurate prediction. Only such a system can provide hemodynamic values that accurately reflect the complex interactions of the whole human system.

Such systems are, however, an enormous technical challenge. Existing attempts at such simulations tend to be very computationally expensive. They typically require considerable amounts of time to run on existing computers, often resulting in simulations that run at best, at the rate of about 1 heart beat per minute.

What is needed is a full-system, cardiovascular simulation and prediction method that can predict the consequences of surgical or medicinal interventions sufficiently accurately, but that can run in real, or quasi-real time, on existing computers. Such a system would be of enormous value in assisting clinicians in real world operating theaters or emergency rooms.

BRIEF SUMMARY OF THE INVENTION

An inventive system and method is disclosed that provides, in real-time, a closed-loop, complete body hemodynamic simulation of a patient undergoing a surgical procedure.

This may, for instance, be done by using a representation of the human blood circulation that, while complex enough to provide an accurate simulation for any condition that may be encountered in an operating theater, may be simple enough to run on existing computers in real, or quasi-real time, i.e., a cycle of calculation representing one heartbeat may occur in the time it takes for a human heart to beat once, i.e., about 1 second.

A clinician may then use the system to predict the result of an intended intervention, and, by observing the predicted hemodynamic data that may be displayed in the operating theater on a suitable screen, see, in a very short time, whether or not the intended intervention is appropriate, and then proceed accordingly.

In a preferred embodiment, the system may include a hemodynamic simulation software module operable on a computational device that may be functionally connected to an image display device. The module may be provided with a first, patient specific, parameter file that may include a patient specific general data file and a patient specific hemodynamic data file.

Using these, the module may proceed to calculate cycles of data, each of which may represent one heartbeat. This data may be in the form of a comprehensive cardiovascular status file, that may present the status of relevant hemodynamic parameters derived based on the patient's entire circulatory system, as modeled mathematically using a simplified, but comprehensive, representation of the human blood circulation system.

The clinician may, for instance, simulate an intended cardiovascular influencing event. This event may range from, a mechanical event such as tilting the operating table to lower the patient's head, to a medical event such as a change in a dose of drug being administered, to a surgical event, such as making an incision at a particular place in the patient.

The event may, for instance, be selected by the clinician from a menu on a touch screen. Selection of an event may result in an appropriate event simulating data file being provided to the hemodynamic simulation software module. The module may then proceed to calculate, in real time, a cycle-by-cycle series of undated patient parameter status files. These comprehensive cardiovascular status files may contain data representative of a predicted status of relevant hemodynamic parameters based on the patient's entire circulatory system, and may effectively chart, heartbeat at a time, the predicted hemodynamic consequences of the intended intervention, including the effect of natural compensatory mechanisms. By observing the predicted outcome of the intended intervention, the clinician may choose to proceed to intervene, or to modify the intervention, and make further predictions.

In a preferred embodiment, the hemodynamic simulation software module may consist of a combination of 1-D mathematical models, and lumped parameter models, that may be supplied, or populated, with suitable parameters. These models and data, based on a simplified, but comprehensive, representation of the human blood circulation system, may provide results in the form of standard hemodynamic parameters that may be derived from input representative of the patient's entire circulatory system. In this way, sufficiently accurate predictions may be made in real time for any events that may typically occur in an operating theater setting.

As described in detail below, the 1D models may be first order, non-linear, hyperbolic partial differential equations linking quantities such as blood density, vessel frictional forces, vessel cross-section, gravity, vessel elastic transmural pressure and vessel stiffness, to blood pressure as function of time Lumped parameter models are a well-known mathematical method in fluid dynamics, where, by using, for instance, the analogies of fluid flow to electrical current, fluid pressure to electrical voltage, and fluid storage to electrical capacitance, fluid systems can be described and visualized using standard electrical graphical elements, and mathematically analyzed using ordinary differential equations having forms similar to those used in electronics.

As described in more detail below, lumped parameter models of elements of the circulation system, including the constituent components of the heart, and number of artery-to-vein blood flows, or blood circulations, may be used to mathematically represent the human blood circulation system in sufficient detail to sufficiently accurately simulate a patient undergoing a surgical procedure in an operating theater environment, while being simple enough to run in real-time on existing computers.

As described in more detail below, the results of the simulation may take the form of cardiovascular status files that may contain hemodynamic parameters that may be well-known to trained clinicians such as, but not limited to, systolic and diastolic arterial blood pressures; systolic and diastolic, right and left, ventricular pressures; arterial and venous oxygen saturations, and oxygen delivery, consumption and extraction.

Therefore, the present invention succeeds in conferring the following, and others not mentioned, desirable and useful benefits and objectives.

It is an object of the present invention to provide a reliable and accurate aid for operating room clinicians performing cardiovascular surgery.

It is another object of the present invention to provide a system for clinicians to predicate the hemodynamic consequences of possible interventions on specific patients in real-time.

DETAILED DESCRIPTION OF THE INVENTION

Figure 1:
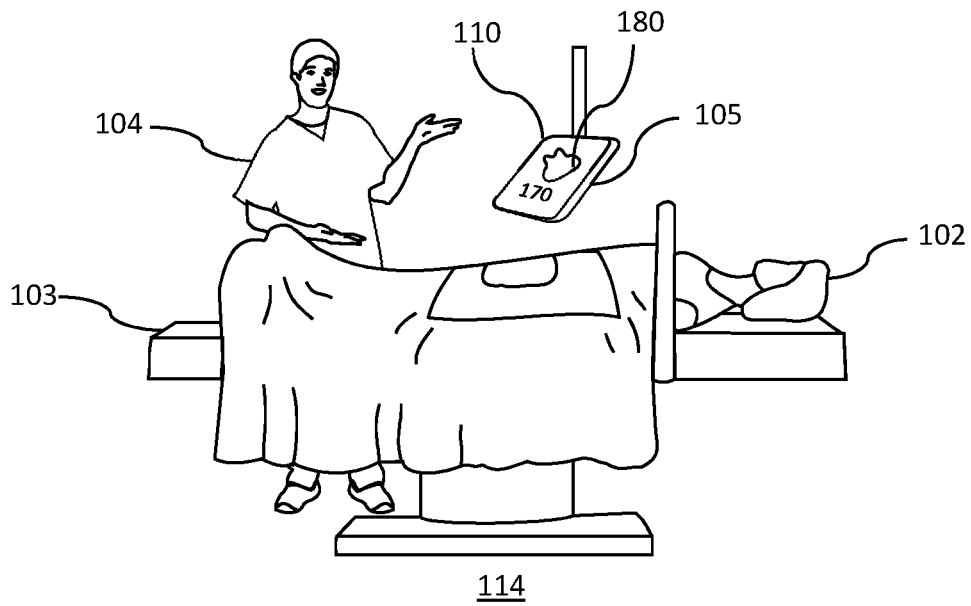
FIG. 1 shows a schematic drawing representative of a patient undergoing a surgical procedure.

The preferred embodiments of the present invention will now be described in more detail with reference to the drawings in which identical elements in the various figures are, as far as possible, identified with the same reference numerals. These embodiments are provided by way of explanation of the present invention, which is not, however, intended to be limited thereto. Those of ordinary skill in the art may appreciate upon reading the present specification and viewing the present drawings that various modifications and variations may be made thereto without departing from the spirit of the invention.

FIG. 1 shows a schematic drawing representative of a patient undergoing a surgical procedure 114.

As shown in FIG. 1, a patient 102 may be situated on an operating table 103 in an operating room, or theater, in order that a clinician 104, who may, for instance, be a trained surgeon, may perform a surgical procedure. There may also be an image display device 110 located within the operating room on which the clinician 104 may see alpha-numeric and/or graphics 180 representative of a medical status of the patient. This image display device 110 may be functionally connected to patient monitoring devices as well as, or instead, to a computational device 105 that may provide relevant information. In a preferred embodiment of the present invention, the computational device 105 may provide patient status simulations that may aid the clinician 104 in making intervention choices, as discussed in more detail below.

In performing surgery on a patient's internal organs, it has become common to use laparoscopic, or minimally invasive, surgery. Laparoscopic surgery, in which surgery is performed through small incisions, may have the benefits over conventional open procedures, of reduced tissue trauma, reduced post-operative pain, lower risk of wound complication, shorter hospital stays, more rapid recovery and reduced costs. There are, however, risks. To optimize laparoscopic visualization and access, it is common practice to place the patient in a steep head down position, the so-called Trendelenburg position, and to inflate access organs, typically the stomach, using pressurized gas. Both tilting the patient and abdominal insufflation can cause adverse physiologic effects on the patient, that may be reflected in hemodynamic changes that may be damaging to the patient, especially if the tilting and insufflation are of long duration. The consequences of such procedures or events, may be further complicated by other factors such as, but not limited to, the effects of drugs used as surgical anesthetics, the use of artificial ventilation to assist breathing, and the body's natural compensatory mechanisms, or a combination thereof.

Figure 2:
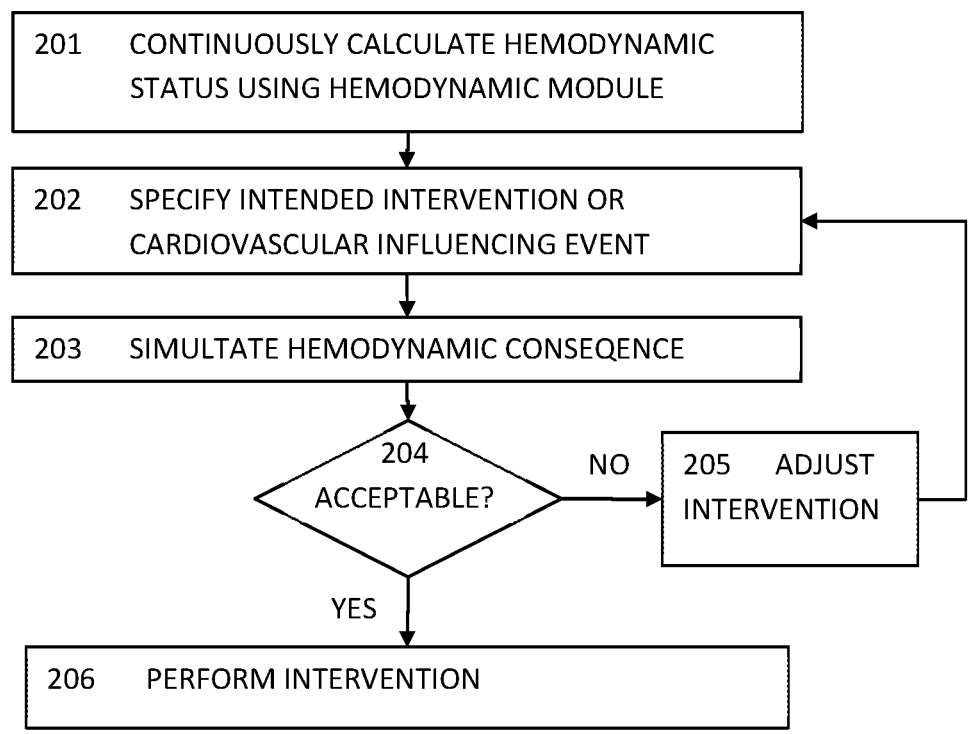
FIG. 2 shows a schematic flow diagram linking representative steps of one embodiment of the present invention.

FIG. 2 shows a schematic flow diagram linking representative steps of one embodiment of the present invention.

In Step 201 "CONTINUOUSLY CALCULATE HEMODYNAMIC STATUS USING HEMODYNAMIC MODULE", a programed software module, operating on a computational device, may provide a comprehensive cardiovascular status file that may contain data in the form of relevant, well-known hemodynamic parameters representative of a hemodynamic status of the patient that may be based on the patient's entire circulatory system.

This may be done by, for instance, a suitably programed hemodynamic simulation software module, that may be operable on a standard, or existing computational device. The module may be programmed to provide a real-time, closed-loop, complete body hemodynamic simulation of a patient undergoing a surgical procedure. During a surgical procedure, certain simplifying assumptions may be made about the patient's body, such as, but not limited to, that the patient may have both legs straight, extended and not moving relative to each other or to the rest of the body; that both arms may be straight, extended and not moving relative to each other; and, that the patient may be lying flat, with no bending of the body or of the head; or some combination thereof. Because of theses assumptions, it may be possible to model the patient's a hemodynamic status using a simplified, but comprehensive, representation of a human blood circulation system as shown in, for instance, FIG. 3. Within these assumptions, such a representation may be used to provide output in the form of relevant hemodynamic parameters that are sufficiently accurate to predict surgical interventions, and may be based on input from the patient's entire circulatory system.

The necessary calculations may be accomplished by, for instance, providing the hemodynamic simulation software module with a first, patient specific, parameter file that may include a patient specific general data file and a patient specific hemodynamic data file.

The hemodynamic simulation software module, operating on a suitable computing device, may then use these files to calculate a first patent parameter status file that may include a first comprehensive cardiovascular status file that may be representative of a first hemodynamic status of the patient at a first point in time, based on patient's entire circulatory system.

These calculations may then proceed to provide continuous cycles of data, each cycle of which may represent one heartbeat of the patient's heart. On each cycle a new comprehensive cardiovascular status file may be generated that may be representative of the hemodynamic status of the patient's entire circulatory system during that heartbeat.

In Step 202 "SPECIFY INTENDED INTERVENTION OR CARDIOVASCULAR INFLUENCING EVENT", the clinician may, for instance, simulate an intended cardiovascular influencing event.

This event to be simulated may range from, a mechanical event such as tilting the operating table to lower the patient's head, to a medical event such as a change in a dose of drug being administered, to a surgical event, such as making an incision at a particular place in the patient, or some combination thereof.

The event may, for instance, be selected by the clinician from a menu on a suitable data input device such as, but not limited to, a touch screen. Selection of an event may result in an appropriate event simulating data file being provided to the hemodynamic simulation software module.

In Step 203 "SIMULATE HEMODYNAMIC CONSEQUENCE", the hemodynamic simulation software module may then proceed to calculate, in real, or quasi-real, time, a cycle-by-cycle series of undated patient parameter status files. These comprehensive cardiovascular status files may contain data representative of a predicted status of relevant hemodynamic parameters based on the patient's entire circulatory system, and may effectively chart, heartbeat at a time, the predicted hemodynamic consequences of the intended intervention, including the effect of natural compensatory mechanisms.

In Step 204 "ACCEPTABLE?" the clinician may observe the predicted outcome of the proposed intervention, that may, for instance be being displayed as alpha-numeric symbols and/or graphics representative of one or more of the well-known, relevant hemodynamic parameters, on a suitable image display device, such as, but not limited to, to a video screen, that may be situated in the operating theater. On viewing the predicted outcome, as conveyed by the predicted hemodynamic parameters, the trained clinician may then use their judgment as to whether or not the proposed intervention is acceptable or not.

If the clinician decides that the predicted outcome is not acceptable, the system may proceed to Step 205 "ADJUST INTERVENTION".

By observing the predicted outcome of the intended intervention, the clinician may, if it appears to provide a favorable outcome, choose to proceed to Step 206 "PERFORM INTERVENTION" and actually preform the intended intervention.

If, however, the simulation predicts that the intervention will result in a dangerous, or otherwise unacceptable outcome, the clinician may choose to proceed instead to Step 205 "ADJUST INTERVENTION". In this step the clinician may opt to forgo the intervention, or to modify it, or to see if an alternate intervention may be more appropriate. Having decided on what adjustment of the intervention is appropriate, the system may return to Step 202 so that the proposed adjusted event may be simulated. This may require initially returning to the hemodynamic state prior to the previous event simulation before beginning the simulation of the proposed adjusted intervention event.

Figure 3:
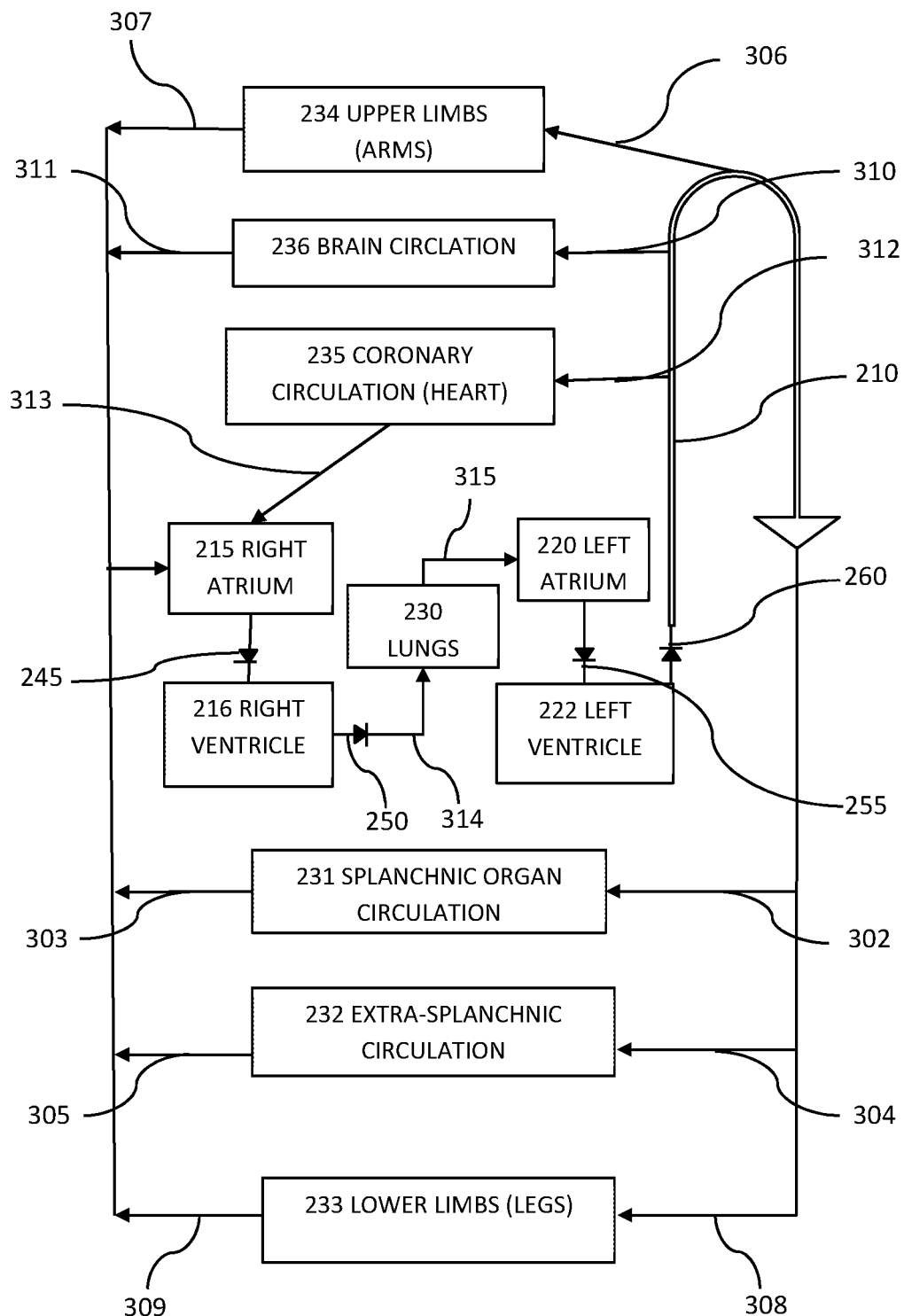
FIG. 3 shows a schematic diagram of a simplified representation of a human blood circulation system.

FIG. 3 shows a schematic diagram of a simplified representation of a human blood circulation system 116.

The human blood system as represented in FIG. 3 may be designed to be sufficiently inclusive so as to be able to provide calculations that are sufficiently accurate to simulate hemodynamic properties of a patient undergoing surgery in an operating room environment. In such an environment, certain simplifying assumptions may be made about the patient's body, such as, but not limited to, that the patient may have both legs straight, extended and not moving relative to each other or the rest of the body; that both arms may be straight, extended and not moving relative to each other; and, that the patient may be lying flat, with no bending of the body or of the head; or some combination thereof. Because of these assumptions, it may be possible to accurately model the patient's a hemodynamic status using a simplified, but comprehensive, representation of a human blood circulation system as shown in FIG. 3.

The details of the elements of FIG. 3 are discussed more fully below in conjunction with FIG. 6.

Figures 4, 5:
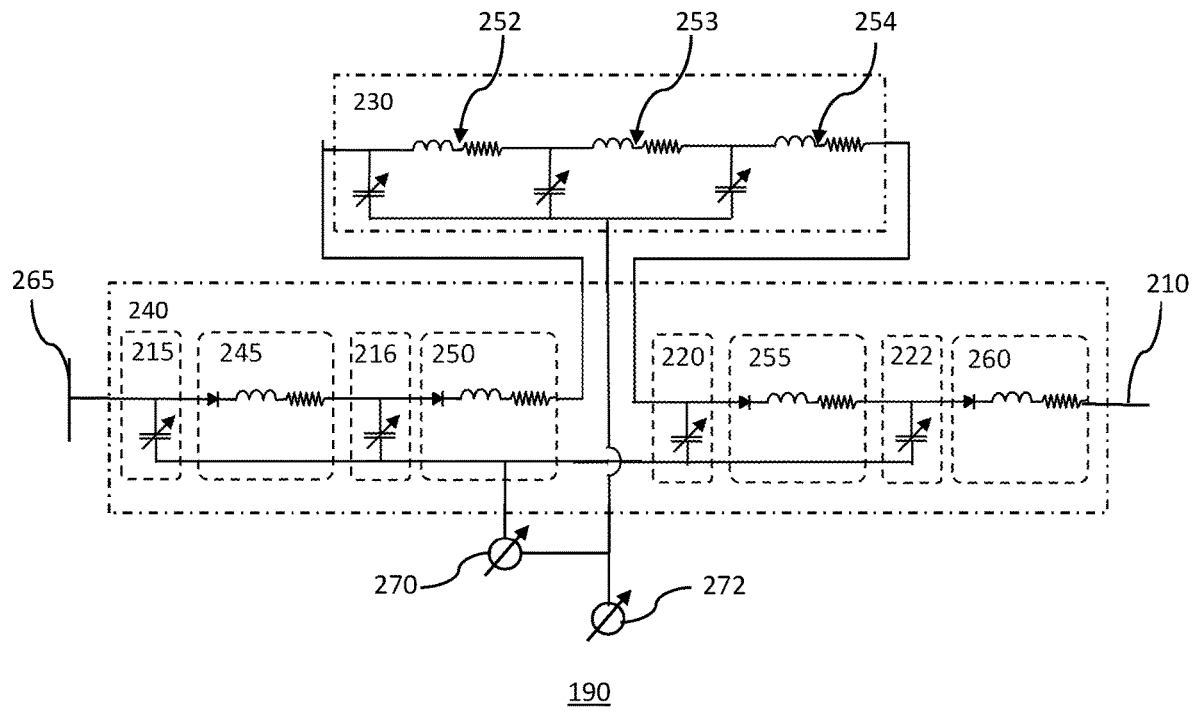
FIG. 4 shows a schematic representation of a lumped parameter model of human heart and lung blood circulation.
FIG. 5 shows an algebraic representation of a 1D mathematical model.

FIG. 4 shows a schematic representation of a lumped parameter model of heart and lung blood circulation.

Lumped parameter models are a well-known mathematical method in fluid dynamics. Using the analogies of, for instance, fluid flow to electrical current, fluid pressure to electrical voltage, and fluid storage to electrical capacitance, fluid systems may be described and visualized using the same standard electrical graphical elements used in drawing electronic circuits. Similarly, fluid flow may be mathematically analyzed using ordinary differential equations having forms analogous to those used in electronic engineering.

As shown in FIG. 4, the heart 240 may be represented by its four principle constituent chambers, i.e., the right atrium 215, the right ventricle 216, the left atrium 220 and the left atrium 220, each of which is shown using the electronic symbol for a variable capacitor. These four chambers are shown linked by four valves, namely the tricuspid valve 245, the pulmonary valve 250, the mitral valve 255 and the aortic valve 260. Each of these valves is represented by a combination, in series, of a diode, and inductor and a resistor.

The fluid differential equation associated with a capacitor is given by:

$$q = C\frac{dp}{dt} \quad (1)$$

in which q represents flow, p represents pressure difference across the element, t is time, and C is the volume of fluid.

The analogous electric differential equation is:

$$i = C\frac{dv}{dt} \quad (2)$$

in which i represents current, v represents voltage difference across an element, and C represents the charge, or volume of electrons.

As show in FIG. 4, the lumped parameter model 190 of the heart/lung circulation shows blood flowing from the venae cavae 265 into the right atrium 215, then on through the tricuspid valve 245 to the right ventricle 216, from where it is pumped through the pulmonary valve 250 to the pulmonary artery 252. Each of the valves is shown represented by a combination in series of a diode, an inductor and a resistor.

The diode primarily represents the unidirectional flow of a fluid in analogy to unidirectional flow of current in an electrical circuit.

The electrical property of inductance is due to the induced magnetic field caused by a changing current flow, and may be expressed by the differential equation:

$$v = L\frac{di}{dt} \quad (3)$$

in which the inductance L links the changing current i to the voltage v.

The analogous concept in fluid dynamics is inertance, which is a measure of the pressure difference in a fluid that is required to cause a unit change in the rate of change of volumetric flow-rate with time. Inertance, which may be thought of as encapsulating the momentum and kinetic energy of a fluid, may be expressed by the differential equation:

$$p = I\frac{dq}{dt} \quad (4)$$

in which the inertance i links the changing flow q to the pressure difference p.

Just as resistance has a linear link to voltage via Ohm's law in electrical circuits, the flow q of a fluid may, under certain conditions, be linked to the pressure difference p, via the simple equation:

$$p = qR \quad (5)$$

The equations and circuits detailed above may be used for accurate simulation of blood flow in the heart by using appropriate known values and units. Typical values for the necessary constants and coefficient to represent the human heart are detailed in, for instance, U.S. Provisional Patent Application Ser. No. 62/523,445 filed Jun. 22, 2017 entitled "Global Multiscale Human Circulation Simulator", the contents of which are fully incorporated herein by reference.

As shown in FIG. 4, blood from the pulmonary artery 252 the flows into the lungs, and may be modeled as a pulmonary circulation 230 lumped parameter model. The pulmonary circulation 230 may be split into three sections, the pulmonary artery 252, the pulmonary capillaries 253 and the pulmonary veins 254. Each of these three sections may be represented in a lumped parameter model by a combination of a variable capacitor, an inductor and a resistor, linked as shown in FIG. 4.

From the pulmonary veins 254, blood may flow into the left atrium 220 and on into the right ventricle 222 via the mitral valve 255. From the right ventricle 222, blood may be pumped into the ascending aorta 210 via the aortic valve 260, all of which may be modeled via lumped parameter elements having the appropriate values expressed in appropriate units.

In addition to the blood flow components, the lumped parameter model 190 shown in FIG. 4 includes a pericardium pressure 270 and a intrapleural pressure 272.

The pericardium is a double-walled sac that encloses the pericardial cavity. It contains the heart and the roots of the great vessels, i.e., the vena cava, the pulmonary arteries and veins, and the aorta, surrounding them. The pericardium may be filled with pericardial fluid that may provide, among other benefits, lubrication for the heart.

The intrapleural pressure, also called intrathoracic pressure, depends on the ventilation phase, atmospheric pressure, and the volume of the intrapleural cavity. The intrapleural pressure may, for instance, be driven by the action of the diaphragm, and external intercostal muscles, i.e., the muscles that connect the ribs and help move the chest wall.

The pressures exerted by these structures typically affect the blood flow in the heart and lungs, and may need to accounted for to obtain an accurate model of the overall blood flow.

FIG. 5 shows an algebraic representation of a 1D mathematical model 185. 1D models are mathematical models may, for instance, be first order, non-linear, hyperbolic partial differential equations linking quantities such as blood density, vessel frictional forces, vessel cross-section, gravity, vessel elastic transmural pressure and vessel stiffness, to blood pressure as function of time.

A mathematical model of blood flowing through the body can be very complex. However, by making a number of assumptions that may be reasonable under operating room conditions, the mathematical model may be reduced to a first order, non-linear, hyperbolic partial differential equation, i.e., an equation that, if the main variable and its first time derivative are arbitrarily specified at time t=0, then there exists a solution for all time t.

For blood flow, the assumptions may include, but are not necessarily limited to, that blood is a Newtonian liquid, i.e., the viscous stresses arising from its flow, at every point, are linearly proportional to the local strain rate; that the flow is laminar and axisymmetric along the vessel; and that the radius of the vessels are small compared to a characteristic wavelength of any wave propagating in the system.

Using such assumptions, and applying the principles of conservation, including those of mass and momentum, an algebraic representation of blood flow through a vessel may be obtained that may be represented as shown in FIG. 5.

In the algebraic representation of blood flow of FIG. 5, the flow U is shown as represented by a first order, non-linear, hyperbolic partial differential equation 186:

$$\partial_t U + \partial_x L(U) = G(U), \quad (6)$$

in which U, the flow, is a function of both time and axial distance along the vessel 187, that may further be expressed using the notation 188:

$$U = \begin{bmatrix} A \\ Q \end{bmatrix} \quad (7)$$

where A represents the cross-sectional area of the vessel, and Q represents the volume flow rate of the blood, and where Q may be linked to A as being equal to the product of A and u, u being the cross-sectional, average axial velocity of the blood flow.

L(U) represents a function of U, that may be further expressed using the additional notation 189:

$$L(U) = \begin{bmatrix} Q \\ \frac{\kappa Q^2}{A} \end{bmatrix} \quad (8)$$

In which k represents a velocity profile which may, under assumptions such as, but not limited to, axisymmetric, laminar flow, involving non-slip conditions, be reduced to a single number that may be measured experimentally.

G(U) represents a further function of U that may be further expressed using the supplementary notation 191:

$$G(U) = \begin{bmatrix} 0 \\ -\frac{A}{\rho}\frac{\partial p}{\partial x} - \frac{f}{\rho} - gA\eta_x \end{bmatrix} \quad (9)$$

in which p is the average internal pressure over a cross-section of the vessel, and is a function of both time, t, and distance along the vessel, x; f is the friction force per unit length of the vessel; $\rho$ is the density of blood; $\eta$ is a coordinate perpendicular to the Earth's surface, that accounts for the gravitational forces due to the presence of gravity acceleration g.

The system of equations represented above may be closed using a suitable pressure-area relationship for the vessels, as described in more detail in, for instance, U.S. Provisional Patent Application Ser. No. 62/523,445 filed Jun. 22, 2017 entitled "Global Multiscale Human Circulation Simulator", the contents of which are fully incorporated herein by reference, and which also describes methods of solving the system of equations, including methods of numerical solution that may be applicable.

The solution of the equations may also require details of the mechanical properties of the vessels, such as, but not limited to, the Youngs modulus of the vessel walls so that transmural pressures for the veins and arteries may be accurately incorporated into the model and accounted for.

Figure 6:
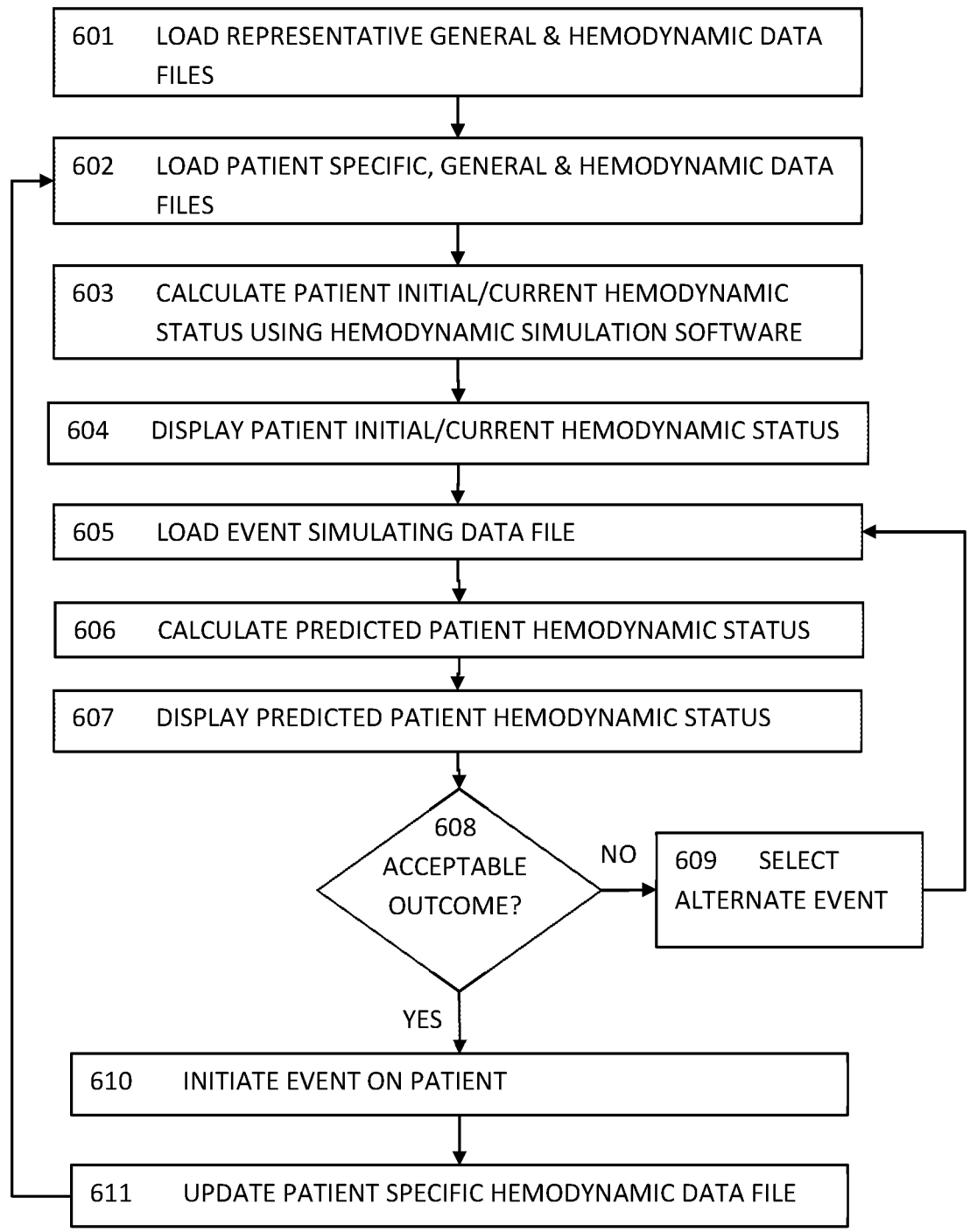
FIG. 6 shows a schematic flow diagram linking representative steps of one embodiment of the present invention.

FIG. 6 shows a schematic flow diagram linking representative steps of one embodiment of the present invention.

In Step 601 "LOAD REPRESENTATIVE GENERAL & HEMODYNAMIC DATA FILES", data files may be loaded into the system having values representative of parameters that may be varied in the hemodynamic simulation software module such as, but not limited to, the local gravitational constant, Young's modulus of human vessel walls, and the average density of human blood, or some combination thereof. These may, for instance, be global modal variables.

In Step 602 "LOAD PATIENT SPECIFIC, GENERAL & HEMODYNAMIC DATA FILES", data may be loaded into the system having values representative of parameters specific to the patient being modeled. The general data may, for instance, include data such as, but not limited to, the patient's age, weight, height, gender, and ethnicity, or some combination thereof.

The patient specific hemodynamic data may include laboratory measured values of the patient, such as, but not limited to, arterial systolic and diastolic blood pressure (BP, SBP, DBP); mean arterial pressure (MAP); right atrial pressure (RAP); central venous pressure (CVP); right ventricular pressure, systolic and diastolic (RVP, RSVP, RDVP); pulmonary artery pressure, pulmonary artery systolic pressure and pulmonary artery diastolic pressure (PAP, PASP, PADP); mean pulmonary artery pressure (MPAP); pulmonary artery occlusion pressure (PAOP); left atrial pressure (LAP); cardiac output (CO); cardiac index (CI), stroke volume, stroke volume index and stroke volume variation (SV, SVI, SVV); systemic vascular resistance (SVR); systemic vascular resistance index (SVRI); pulmonary vascular resistance (PVR); left ventricular stroke work index (LVSWI,); right ventricular stroke work index (RVSWI), coronary artery perfusion pressure (CPP); right ventricular end-diastolic volume (RVEDV); right ventricular end-diastolic volume index (RVEDVI); right ventricular end-systolic volume (RVESV); right ventricular end-systolic volume index (RVESVI); right ventricular ejection fraction (RVEF); cardiac power (CPO); and cardiac power index (CPOI).

They may also, or instead, include respiratory related hemodynamic, laboratory measured values of the patient, such as, but not limited to, arterial oxygen saturation (SaO2); central venous saturation (ScvO2); mixed venous saturation (SvO2); arterial oxygen content (CaO2); venous oxygen content (Cv02); A-V oxygen content difference; oxygen delivery (DO2); oxygen delivery index (DO2I); oxygen consumption (V02); oxygen consumption index (VO2I); oxygen extraction ratio (O2ER); and oxygen extraction index (O2EI).

In Step 603 "CALCULATE PATIENT INITIAL/CURRENT HEMODYNAMIC STATUS USING HEMODYNAMIC SIMULATION SOFTWARE", the hemodynamic simulation software module. operating on a suitable computing device, may now use this data to calculate a first patient parameter status file that may include a first comprehensive cardiovascular status file that may be representative of a first hemodynamic status of said patient's entire circulatory system at a first point in time.

These calculations may then be used to provide continuous cycles of data, each cycle of which may represent one heartbeat of the patient's heart. On each cycle a new comprehensive cardiovascular status file may be generated that may be representative of the hemodynamic status of the patient's entire circulatory system during that heartbeat.

The calculations may, for instance, obtain solutions to a system that may include both first order, non-linear, hyperbolic partial differential equations and lumped parameter models of the sort described above.

The veins and arteries modeled by the first order, non-linear, hyperbolic partial differential equations may, for instance, include those shown in the simplified representation of a human blood circulation system shown above in FIG. 3.

As shown in FIG. 3, the veins and arteries modeled may, therefore, include vessels functionally connected to the heart such as, but not limited to, an ascending aorta 210, or aortic arch; one or more splanchnic arteries 302; one or more splanchnic veins 303; one or more extra-splanchnic arteries 304; one or more extra-splanchnic veins 305; one or more lower limb skeletal muscle arteries 308; one or more lower limb skeletal muscle veins 309; one or more upper limb skeletal muscle arteries 306; one or more upper limb skeletal muscle veins 307; one or more carotid arteries 310; one or more jugular veins 311, one or more of the coronary circulation, arterial 312; one or more of the coronary circulation; venous 313; the pulmonary circulation, arterial 314; and the pulmonary circulation; venous 315.

The splanchnic arteries 302 may, for instance, be one or more of the celiac trunk, the inferior mesenteric artery, the superior mesenteric artery, the splenic artery, the common hepatic artery, and the renal artery, or some combination thereof.

The splanchnic veins 303 may, for instance, be one or more of the hepatic veins, the inferior vena cava, the superior vena cava, the heptic veins, and the abdominal vena cava, or some combination thereof.

The extra-splanchnic arteries 304 may, for instance, be one or more of the renal artery, the inferior mesenteric artery, the testicularis artery, the common iliac artery, the internal iliac artery, and the inferior epigastric artery, or some combination thereof.

The extra-splanchnic veins 305 may, for instance, be one or more of the renal veins, the abdominal vena cava, the testicularis vein, the common iliac vein, and the internal iliac vein, or some combination thereof.

The upper limb skeletal muscle arteries 306 may, for instance, be one or more of the subclavian arteries, and the vertebral arteries, or some combination thereof.

The upper limb skeletal muscle veins 307, may, for instance, be one or more of the subclavian veins, the external jugular veins, the internal jugular veins, and the inferior thyroid vein, or some combination thereof.

The lower limb skeletal muscle arteries 308 may, for instance, be one or more of the external iliac artery, the common iliac artery, the internal iliac artery, the femoral circumflex artery, or some combination thereof.

The lower limb skeletal muscle veins 309 may, for instance, be one or more of the common iliac vein, the external iliac vein, the internal iliac vein, or some combination thereof.

The carotid arteries 310 may, for instance, be one or more of the common carotid arteries, the vertebral arteries, the internal carotid arteries, and the external carotid arteries, or some combination thereof.

The jugular veins 311 may, for instance, be one or more of the internal jugular veins, the external jugular veins, and the inferior thyroid veins, or some combination thereof.

The coronary circulation, arterial 312 may, for instance, be one or more of the coronary arteries.

The coronary circulation; venous 313, may for instance, be one or more of the coronary sinus.

The pulmonary circulation, arterial 314, may, for instance, be one or more of the pulmonary arteries.

The pulmonary circulation; venous 315, may, for instance, be one or more of the pulmonary veins.

The circulatory systems modeled by lumped parameter models may, for instance, include those shown in FIG. 3.

As shown in FIG. 3, the circulatory systems may, for instance, include systems such as, but not limited to, a heart's right atrium 215, right ventricle 216, left atrium 220, and right ventricle 222, a pulmonary circulation 230; a splanchnic 231 artery-to-vein blood flow; an extra-splanchnic 232 artery-to-vein blood flow; a lower limbs 233 artery-to-vein blood flow; an upper limbs 234 artery-to-vein blood flow; a coronary circulation 235; and, a brain blood circulation 236, or some combination thereof.

In solving the systems of equations described above, the contraction and relaxation of the heart may be modeled as a time-varying elastance function as derived from well-known myocardial elastance theory. This is described in more detail in, for instance, U.S. Provisional Patent Application Ser. No. 62/523,445 filed Jun. 22, 2017 entitled "Global Multiscale Human Circulation Simulator", the contents of which are fully incorporated herein by reference.

One equation that may be used to the contraction and relaxation of the heart may be represented algebraically as:

$$P_{ch}(t) = P_{e,ch} + E(t)(V_{ch} - V_{ch,0}) + S\frac{dV_{ch}}{dt} \quad (10)$$

where $P_{ch}$ represents pressure in the chamber, $P_{e,ch}$ represents an unstressed pressure of the chamber, $E(t)$ is a time varying elastance function, $V_{ch}$ represents the volume of the chamber, $V_{ch,0}$ represents the unstressed volume of the chamber, and $S$ represents the viscoelasticity coefficient of the cardiac walls.

As described in more detail in the above mentioned reference, account may also be taken of the relationship between vertricular systolic duration, ventricular isovolumic relaxation, and heart rate by means of parameters derived from curve fitting to experimental data.

The respiratory system, including gas transport in the lungs, and gas transport in the cardiovascular system, may be modeled including oxygen and carbon dioxide dissociation.

The effect of the autonomic nervous system may also be incorporated into the model of the cardio vascular system by, for instance, using experimental data regarding the baroreflex. The baroreceptors may, for instance, respond to pressure in the atria of the heart, the vena cava, and, most, sensitively, in the carotid sinuses and aortic arch, by altering the heart rate in an attempt to maintain constant blood pressure. The negative feedback loop provided by the barorelex in which rising pressure may tend to lower the heart rate, and vice-versa, may be incorporated using linear first order equations that effectively model experimental data.

The combined system model described above may, for instance, be solved using a combination of numerical methods.

In one preferred embodiment of the present invention, one, or more, of the 1D first-order, nonlinear hyperbolic equations may be solved using an augmented Roe solver in which wave celerities are defined using an approximate Jacobian matrix.

The result of these calculations may, for instance, be cardiovascular status files having parameters representing updates of the patient specific hemodynamic data such as, but not limited to, to updates of the laboratory measured values described above.

The results may, therefore, include one or more arterial circulation parameters, such as, but not limited to, systolic and diastolic arterial blood pressures; one or more cardiac parameters, comprising heart rate; and systolic and diastolic, right and left, ventricular pressures; and one or more respiration parameters, comprising arterial and venous oxygen saturations.

In a preferred embodiment, the results may also include current patient data such as, but not limited to, mean arterial pressure, systemic vascular resistance, net arterial compliance and coronary artery perfusion; right atrial pressure, central venous pressure, stressed volume and unstressed volume; cardiac output; cardiac index; stoke volume; stroke volume index; and right ventricular, end-diastolic and end-systolic volume; and left and right ventricular stroke work; systolic, diastolic and mean pulmonary artery pressure; and oxygen delivery, consumption and extraction, or some combination thereof.

In Step 604 "DISPLAY PATIENT INITIAL/CURRENT HEMODYNAMIC STATUS" the results being generating on a heartbeat at a time cycle, may be displayed on a suitable display device in a form that may be of a clinician's choosing, i.e., the clinician may only be interested in monitoring a subset of the output parameters available, and may wish to focus on how those will be effected by any simulated intervention.

Step 605 "LOAD EVENT SIMULATING DATA FILE".

In this step, the clinician may, for instance, simulate an intended cardiovascular influencing event. This event may range from, a mechanical event such as tilting the operating table to lower the patient's head, to a medical event such as a change in a dose of drug being administered, to a surgical event, such as making an incision at a particular place in the patient.

The event may, for instance, be selected by the clinician from a menu on a touch screen. Selection of an event may result in an appropriate event simulating data file being provided to the hemodynamic simulation software module.

Step 606 "CALCULATE PREDICTED PATIENT HEMODYNAMIC STATUS". In this step, the hemodynamic simulation software module may, using the models and methods described above, proceed to calculate, in real time, a cycle-by-cycle series of undated patient parameter status files. These comprehensive cardiovascular status files may contain data representative of a predicted status of relevant hemodynamic parameters based on the patient's entire circulatory system, and may effectively chart, heartbeat at a time, the predicted hemodynamic consequences of the intended intervention, including the effect of natural compensatory mechanisms.

Step 607 "DISPLAY PREDICTED PATIENT HEMODYNAMIC STATUS". In this step the relevant simulated values contained in the comprehensive cardiovascular status files calculated in the previous step, may now be displayed to a clinician on an appropriate display device in a manner that may have been determined by the clinician to best suit their needs.

Step 608 "ACCEPTABLE OUTCOME?". In this step, the trained clinician may observe the predicted outcome of the intervention they are proposing, and which is now being simulated in a series of heartbeat by heartbeat cycles. Based on what they see, and their training, the trained clinician may either decide that the intervention will achieve the desired outcome, and therefore proceed to Step 610 "INITIATE EVENT ON PATIENT" and proceed to carry out the intervention. Or, if the predicted outcome does not achieve the desired outcome, or presents an unacceptable risk to the patient, the trained clinician may elect to proceed to Step 609 "SELECT ALTERNATE EVENT". In Step 609, the clinician may elect to change, or modify, the event, or intervention that they want to try. Before trying the new event, they may first elect to go to Step 605, cause a new event file to be loaded, and then observe the predicted outcome of the newly selected intervention.

After the event, or intervention, has been performed on the patient, the system may then proceed to Step 611 "UPDATE PATIENT SPECIFIC HEMODYNAMIC DATA FILE". In this step the patient specific files may be updated to reflect the effect of the event, or intervention, that may have been performed on the patient.

Although this invention has been described with a certain degree of particularity, it is to be understood that the present disclosure has been made only by way of illustration and that numerous changes in the details of construction and arrangement of parts may be resorted to without departing from the spirit and the scope of the invention.

The invention claimed is:

1. A full-system, cardiovascular simulation and prediction method, comprising:
   providing a computational device functionally connected to an image display device;
   providing a hemodynamic simulation software module, operable on said computational device, programmed to provide, cycle by cycle, a real-time, closed-loop, complete body hemodynamic simulation of a patient undergoing a surgical procedure, said simulation accounting directly for effects due to gravitational forces, and for a direction in which said gravitational forces are applied relative to a direction of blood flow in elements of said hemodynamic model;
   providing a first, patient specific, parameter file comprising a patient specific general data file and a patient specific hemodynamic data file;
   calculating, using said computational device, said hemodynamic simulation software module, and said first patient specific parameter file, a first patient parameter status file comprising a first comprehensive cardiovascular status file representative of a first hemodynamic status of said patient's entire circulatory system at a first point in time;
   simulating a proposed cardiovascular influencing event, said event characterized, in part, by a change in direction of applied gravitational forces relative to a direction of blood flow in said patient's blood vessels, by providing an event simulating data file;
   calculating, in real time, a second, undated patient parameter status file, comprising a second comprehensive cardiovascular status file representative of a predicted, second hemodynamic status of said patient's entire circulatory system at a second point in time, said second point in time being at, or after, a time at which said proposed cardiovascular influencing, event would have been implemented; and, displaying on said image display device, one or more alphanumeric symbols, and/or a graphic, representative of said second comprehensive cardiovascular file.

2. The method of claim 1, wherein, said hemodynamic simulation software module comprises, one or more 1D mathematical models of one or more arteries, and, one or more veins, combined with lumped parameter models of one or more constituent components of the heart, and one or more artery-to-vein blood flows, or blood circulations.

3. The method of claim 2, wherein, said 1D models are first order, non-linear, hyperbolic partial differential equations linking blood density, vessel frictional forces, vessel cross-section, a direction of gravitational acceleration relative to a direction of blood flow, vessel elastic transmural pressure and vessel stiffness to blood pressure as a function of time; and said lumped parameter models comprise mathematical models in which blood flow is calculated by analogy to electrical components comprising capacitors, resistors and inductors.

4. The method of claim 3, comprising:
1D mathematical models for:
an ascending aorta functionally connected to a heart; and,
lumped parameter models for:
a right atrium, a right ventricle, a left atrium, and a right ventricle of said heart;
a pulmonary circulation;
a splanchnic artery-to-vein blood flow;
an extra-splanchnic artery-to-vein blood flow;
a lower limbs artery-to-vein blood flow;
an upper limbs artery-to-vein blood;
a coronary circulation; and,
a brain blood circulation, and,
wherein, all of said blood flows are functionally connected to said heart.

5. The method of claim 4, further comprising, 1D mathematical models for:
one or more splanchnic arteries;
one or more splanchnic veins; one or more extra-splanchnic arteries;
one or more extra-splanchnic veins;
one or more lower limb skeletal muscle arteries;
one or more lower limb skeletal muscle veins;
one or more upper limb skeletal muscle arteries;
one or more upper limb skeletal muscle veins;
one or more carotid arteries; and, one or more jugular veins, and,
wherein, all of said arteries and veins are functionally connected to said heart.

6. The method of claim 5 wherein one, or more, of said 1D first-order, nonlinear hyperbolic equations is solved using an augmented Roe solver in which wave celerities are defined using an approximate Jacobian matrix.

7. The method of claim 4, further comprising using pressure data from a carotid sinus and an aortic arch to alter a heart rate in accordance with experimental data modeled by one or more liner first order equations.

8. The method of claim 3, wherein said cardiovascular status files comprise parameters representing:

one or more arterial circulation parameters, comprising systolic and diastolic arterial blood pressures;
one or more cardiac parameters, comprising heart rate, and systolic and diastolic, right and left, ventricular pressures; and
one or more respiration parameters, comprising arterial and venous oxygen saturations.

9. The method of claim 8, wherein said cardiovascular status files further comprise parameters representing:
said one or more arterial circulation parameters, further comprising mean arterial pressure, systemic vascular resistance, net arterial compliance and coronary artery perfusion;
one or more venous circulation parameters, comprising right atrial pressure, central venous pressure, stressed volume and unstressed volume;
one or more cardiac preload, contractility and afterload parameters, comprising cardiac output; cardiac index; stroke volume; stroke volume index; and right ventricular, end-diastolic and end-systolic volume; and left and right ventricular stroke work;
one or more pulmonary hemodynamic parameters, comprising systolic, diastolic and mean pulmonary artery pressure; and
one or more respiration parameters, comprising oxygen delivery, consumption and extraction.

10. A full-system, cardiovascular simulation system, comprising:
a computational device functionally connected to an image display device;
a hemodynamic simulation software module, operable on said computational device, and programmed to provide a real-time, closed-loop, complete body hemodynamic simulation of a patient undergoing a heart related surgical procedures, said simulation accounting directly for effects due to gravitational forces and a direction in which said gravitational forces are applied relative to a direction of blood flow in elements of said hemodynamic simulation software model;
a first, patient specific, parameter file comprising a patient specific general data file, and a patient specific hemodynamic data file;
a first patient parameter status file calculated using said computational device, said hemodynamic simulation software module, and said first patient specific parameter file, said first patient parameter status file comprising a first comprehensive cardiovascular status file representative of a first hemodynamic status of said patient's entire circulatory system at a first point in time;
an event simulating data file comprising data for simulating a cardiovascular influencing event, said event characterized, in part, by a change in direction of applied gravitational forces relative to a direction of blood flow in said patient's blood vessels;
a second, undated patient parameter status file calculated in real time, said second, undated patient parameter status file comprising a second comprehensive cardiovascular status file representative of a predicted, second hemodynamic status of said patient's entire circulatory system at a second point in time, said second point in time being at, or after, a time at which said cardiovascular influencing event would have been triggered; and
a graphic displayed on said image display device, said graphic being representative of said second comprehensive cardiovascular file.

* * * * *